United States Patent [19]

Meguro et al.

[11] Patent Number: 5,278,186

[45] Date of Patent: Jan. 11, 1994

[54] CHROMENE DERIVATIVES, THEIR PRODUCTION AND USE

[75] Inventors: Kanji Meguro, Nishinomiya; Hiroyuki Tawada, Takatsuki; Hitoshi Ikeda, Higashiosaka, all of Japan

[73] Assignee: Takeda Chemical Industries, Ltd., Osaka, Japan

[21] Appl. No.: 671,796

[22] PCT Filed: Feb. 2, 1991

[86] PCT No.: PCT/JP91/00172

§ 371 Date: Apr. 2, 1991

§ 102(e) Date: Apr. 2, 1991

[87] PCT Pub. No.: WO91/12249

PCT Pub. Date: Aug. 22, 1991

[30] Foreign Application Priority Data

Feb. 10, 1990 [JP] Japan .................... 2-29940
May 18, 1990 [JP] Japan .................... 2-129690
Sep. 14, 1990 [JP] Japan .................... 2-244953

[51] Int. Cl.$^5$ .................. A61F 31/355; C07D 311/12
[52] U.S. Cl. .................... 514/457; 549/399
[58] Field of Search .................. 549/399; 514/457

[56] References Cited

U.S. PATENT DOCUMENTS 4,387,105 6/1983 DeVries et al.
4,585,786 4/1986 Berthelon.

FOREIGN PATENT DOCUMENTS 646698 12/1984 Czechoslovakia.
2133007 7/1984 United Kingdom.
2168696 6/1986 United Kingdom.

OTHER PUBLICATIONS

J. Med. Chem., 1986, vol. 29, pp. 1131–1133.

Primary Examiner—Marianne M. Cintins
Assistant Examiner—John Peabody
Attorney, Agent, or Firm—Wegner, Cantor, Mueller & Player

[57] ABSTRACT

A chromene derivative of the formula (I)

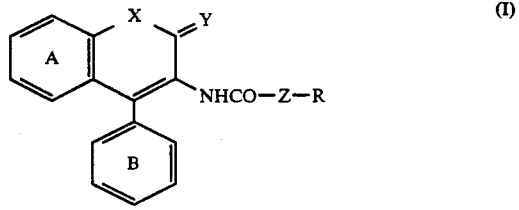

wherein each ring of A and B can have one or more substituents; X is an oxygen atom or sulfur atom, Y is an oxygen or sulfur atom or $H_2$, Z is a bond, —NH— or a saturated or unsaturated lower alkylene group and R is a hydrocarbon radical which is unsubstituted or substituted, or its salt, which is useful as a drug for atherosclerosis.

21 Claims, No Drawings

CHROMENE DERIVATIVES, THEIR PRODUCTION AND USE

BACKGROUND OF THE INVENTION

1. Field of the Invention

This invention relates to novel chromene derivatives, their production and use. The compounds of this invention possess excellent inhibitory action against acyl-CoA: cholesterol acyltransferase (ACAT). Especially, the compounds of this invention inhibit the absorption of cholesterol through the intestinal tract of a mammal and also restrain the accumulation of cholesterol ester at the arterial wall, and accordingly are useful as a drug for preventing and treating hypercholesterolemia, atherosclerosis and various diseases caused thereby (e.g., ischemic cardiac diseases such as myocardial infarction, cerebrovascular disturbance such as cerebral infarction, cerebral apoplexy, etc.).

2. Description of the Prior Art

Japanese Examined Patent Application No. 63(1988)-502348 mentions specifically 4-(3-methoxyphenyl)-3-methylaminochromene. However, compounds in which a urea or an acylamino group is substituted are not prepared in the above Japanese application.

SUMMARY OF THE INVENTION

The inventors of this invention have made various studies on chromene derivatives, and found that new compounds unexpectedly possess potent ACAT inhibitory activity and are useful as a drug for atherosclerosis.

Thus, this invention relates to (1) a chromene derivative of the formula (I):

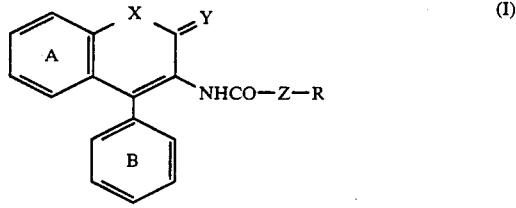

wherein each ring of A and B can have one or more substituents; X is an oxygen atom or sulfur atom, Y is an oxygen or sulfur atom or $H_2$, Z is a bond, —NH— or a saturated or unsaturated lower alkylene group and R is a hydrocarbon radical which is unsubstituted or substituted, or its salt; and (2) an ACAT inhibitory composition comprising a chromene derivative of the formula (I), or its salt.

THE PREFERRED EMBODIMENT OF THE INVENTION

Each of the ring A and B in the formula (I) can have one or more substituents. Examples of the substituents are a halogen atom, an optionally halogenated lower alkyl group, an optionally halogenated lower alkoxy group, an optionally halogenated lower alkylthio group, nitro group, an optionally esterified carboxy group, a $C_{1-3}$ acyloxy (e.g., formyloxy, acetoxy, propionyloxy, etc.), hydroxyl group and a $C_{1-3}$ acyl group (e.g., formyl, acetyl, propionyl, etc.). The halogen atom as the substituent may be fluorine, chlorine, bromine or iodine atom.

The optionally halogenated lower alkyl groups can be straight or branched chain lower alkyl groups of 1-6 carbon atoms and these lower alkyl groups may be substituted with two to five halogen atoms, such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl or 5-trifluoromethylpentyl.

The optionally halogenated lower alkoxy groups and the optionally halogenated lower alkylthio groups can be those formed by the combination of the above mentioned lower alkyl groups or halogenated lower alkyl groups and an oxygen or sulfur atom.

The optionally esterified carboxyl groups may be a carboxyl group and carboxy groups esterified by an alkyl of 1-6 carbon atoms such as methyl, ethyl, propyl, isopropyl, butyl, isobutyl, sec-butyl, tert-butyl, pentyl or hexyl.

The substituent(s) on the rings A and B can be at any position of each ring, and these substituents may be the same or different, and the number of the substituent(s) may be 1 to 4. The suitable position(s) of the substituent(s) are 6-, 7- and/or 8- positions of the chromene nucleus for the ring A, and 2- position for the ring B.

Preferable examples for the ring A are a mono-substituted ring having a substituent of a halogen atom such as fluorine or chlorine atom, a $C_{1-4}$ alkyl group such as methyl, ethyl, propyl or isopropyl at its 6-position, or 6,7-dimethyl, 6,7-difluoro, 6,8-difluoro, 6,7-dichloro, 6,8-dichloro, 6-methyl-7-chloro, 6-chloro-7-methyl and 6-methyl-8-chloro di-substituted ring. Preferable examples for the ring B are a mono-substituted ring having a substituent of a halogen atom such as a fluorine or chlorine atom, $C_{1-4}$ alkyl group such as methyl or ethyl, methoxy group, ethoxy group or methylthio group, or 3,4-dimethyl or 3,4-dimethoxy di-substituted ring.

R in the formula (I) represents a hydrocarbon radical which may have one or more substituents. Examples of the hydrocarbon radicals represented by R are an alkyl, aryl or aralkyl group.

Preferably, the alkyl groups for R are straight, branched or cyclic chain ones having 1-8 carbon atoms, such as methyl, ethyl, propyl, isopropyl, cyclopropyl, butyl, isobutyl, sec-butyl, tert-butyl, cyclopropylmethyl, pentyl, isopentyl, neopentyl, cyclopentyl, hexyl, cyclohexyl, heptyl, cyclohexylmethyl, octyl and the like.

Preferably, the aryl groups for R are those having 6-10 carbon atoms, such as phenyl or naphthyl.

The preferable aralkyl groups for R are those having 7-16 carbon atoms, such as benzyl, 1-phenylethyl, 2-phenylethyl, 1-phenylpropyl, 2-phenylpropyl, 3-phenylpropyl, diphenylmethyl or the like.

These alkyl, aryl and aralkyl groups may have the same or different substituents) in the number of 1 to 5. Preferable substituents are those used for the above-mentioned ring A and ring B.

A phenyl group is preferable for the aryl groups represented by R. This phenyl group may have 1 to 5 substituents such as a halogen atom, alkyl group, alkoxy group or the like, among which a halogen atom (e.g., fluorine, chlorine, bromine or iodine atom) is more preferable. Especially, the phenyl group having 1 to 5 chlorine or fluorine atoms is most preferable. Specifically, a 2,4-difluorophenyl group is more preferable.

Preferable alkyl groups to be possessed by the phenyl groups are $C_{1-4}$ alkyl groups such as methyl, ethyl, isopropyl or the like. Especially, 2,6-dimethylphenyl, 2-methyl-6-isopropylphenyl or 2,6-diisopropylphenyl are preferable ones as R.

Preferable alkoxy groups to be possessed by the phenyl groups are $C_{1-4}$ alkoxy groups such as methoxy, ethoxy or the like. Especially, 2,6-dimethoxyphenyl is preferable as R.

In addition, R is preferably a phenyl group having the aforementioned $C_{1-4}$ alkyl or $C_{1-4}$ alkoxy group as well as a hydroxy group or $C_{1-3}$ acylated (e.g., formyl or acetyl) hydroxy group, especially such as 4-acetoxy-3,5-dimethylphenyl, 4-hydroxy-3,5-dimethylphenyl, 4-acetoxy-3,5-dimethoxyphenyl or 4-hydroxy-3,5-dimethoxyphenyl.

Benzyl groups or 1-phenylethyl groups are preferable for the aralkyl groups represented by R. Preferably, 1 to 5 halogen atoms, alkyl groups, alkoxy groups or the like are substituted on the benzene ring of the aralkyl groups. The halogen atom is preferably a fluorine or chlorine. Preferable examples for R are fluorine-substituted aralkyl groups, especially 2,4-difluorobenzyl groups.

Preferable alkyl groups are $C_{1-4}$ alkyl groups such as methyl, ethyl, isopropyl, tert-butyl or the like.

Preferable alkoxy groups are $C_{1-4}$ alkoxy groups such as methoxy, ethoxy or the like.

R is preferably a benzyl having the aforesaid $C_{1-4}$ alkyl or $C_{1-4}$ alkoxy groups as well as a hydroxy group or $C_{1-3}$ acylated (e.g., formyl or acetyl) hydroxy group. Preferable examples of benzyl for R are 4-acetoxy-3,5-dimethylbenzyl, 4-hydroxy-3,5-dimethylbenzyl, 4-acetoxy-3,5-dimethoxybenzyl or 4-hydroxy-3,5-dimethoxybenzyl.

Examples of saturated or unsaturated alkylene groups represented by Z are $C_{1-5}$ alkylenes such as methylene, ethylene, trimethylene,

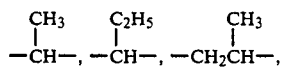

or the like, C2-5 alkenylenes such as —CH=CH—, —CH=CHCH$_2$—, —CH=CH—CH=CH—, or the like, among which a group represented by —(CH$_2$)$_m$— (m is 0,1 or 2) or —CH=CH— is more preferable. Z is preferably a bond, methylene, —CH=CH— or the like. An oxygen atom or sulfur atom is used for X. An oxygen atom is more preferable.

Used for Y is an oxygen, a sulfur or dihydrogen atoms, among which an oxygen atom is more preferable.

The chromene derivative of the formula (I) and its salt can be prepared, for example, by the following methods.

In the case of preparing the compound (I) in which Z is —NH—:

1) The chromene derivative of the formula (I) can be prepared by reacting a compound of the formula (II):

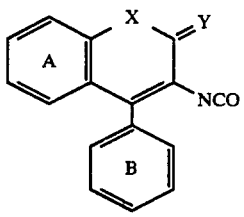

or its salt with a compound of the formula (III):

 (III)

or its salt. The symbols used in the above formulas (II) and (III) have the same meanings as defined above.

2) The chromene derivative of the formula (I) can be prepared by reacting a compound of the formula (IV):

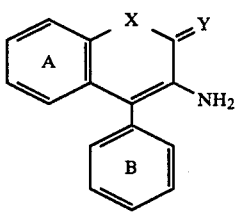

or its salt with a compound of the formula (V):

 (V)

or its salt. The symbols used in the above formulas (IV) and (V) have the same meanings as defined above.

In the case of preparing the compound (I) in which Z is a bond or a saturated or unsaturated lower alkylene group:

3) The chromene derivative of the formula (I) can be prepared by reacting the compound (IV) or its salt with a compound of the formula (VI):

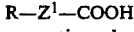 (VI)

or its reactive derivative. In the formula (VI), $Z^1$ is a bond or a saturated or unsaturated alkylene group, and other symbols have the same meanings as defined above.

4) The compound (I) in which Z is an unsaturated alkylene group such as an alkenylene group can be reduced, if necessary, to obtain the chromene derivative of the formula (I) in which Z is an alkylene group.

The above-mentioned methods 1) to 4) will be explained hereinbelow in detail.

1) The compound (II) is conventionally reacted with the compound (III) or its salt (e.g., salts with mineral acids such as hydrochloric acid, sulfuric acid or the like or organic acid salts such as methanesulfonic acid, benzenesulfonic acid, toluenesulfonic acid, oxalic acid, fumaric acid, maleic acid or the like) in a solvent. The solvent to be used may be any solvent, for example, ethers such as ethyl ether, isopropyl ether, tetrahydrofuran, dioxane or dimethoxyethane; aromatic hydrocarbons such as benzene, toluene or xylene; esters such as methyl acetate or ethyl acetate; N,N-dimethylformamide, dimethylsulfoxide or the like.

When the compound (III) is used in the form of an acid salt, use of a deacidifying agent if needed will significantly promote the reaction. The deacidifying agents to be used are preferably tertiary amines such as trimethylamine, triethylamine or N-methylmorpholine, or aromatic amines such as pyridine, picoline or N,N-dimethylaniline. The amount of the amine to be used is about 1 to 5 equivalents, preferably about 1 to 3 equivalents, to the compound (III). The reaction temperature is generally about $-10°$ C. to 180° C., preferably about 0° C. to 120° C. The reaction time is usually about 15 minutes to 24 hours, preferably about 30 minutes to 12 hours. The amount of the compound (III) to be used is about 1 to 5 mol equivalents, preferably about 1 to 3 mol equivalents, to 1 mol of the compound (II).

2) The compound (IV) or its salt (e.g., salts with mineral acids such as hydrochloric acid or sulfuric acid or salts with organic acids such as methanesulfonic acid, benzenesulfonic acid, toluenesulfonic acid, oxalic acid, fumaric acid, maleic acid or the like) is reacted with the compound (V) under the same condition as in the method 1). In case of using the compound (IV) in the form of salt, the deacidifying agent mentioned in the method 1) is used. The amount of the compound (V) is usually about 1 to 5 mol equivalents, preferably about 1 to 3 mol equivalents, to 1 mol of the compound (IV).

3) The compound (IV) or its salt (e.g., salts with mineral acids such as hydrochloric acid or sulfuric acid or with organic acids such as methanesulfonic acid, benzenesulfonic acid, toluenesulfonic acid, oxalic acid, fumaric acid, malenic acid or the like) is reacted with the compound (VI) by using an appropriate condensing agent or after leading the compound (VI) to its reactive derivative before reacting with the compound (IV) or its salt. Examples of such condensing agents are dicyclohexylcarbodiimide (DCC), diethylphosphoryl cyanide (DEPC), diphenylphosphoryl azide (DPPA) or the like. When such a condensing agent is used, the reaction is usually carried out in a solvent (e.g., tetrahydrofuran, dioxane, dimethoxyethane, ethyl acetate, benzene, toluene, N,N-dimethylformamide or dimethylsulfoxide), at about $-10°$ C. to 100° C., preferably at about 0° C. to 60° C., optionally in the presence of a base for accelerating the reaction. The reaction time is usually about 1 to 96 hours, preferably about 1 to 72 hours. The amount of each of the compound (VI) and the condensing agent to be used is about 1 to 5 equivalents, preferably about 1 to 3 equivalents, to the compound (IV) or its salt. Examples of the bases to be used are alkylamines such as triethylamine, or cyclic amines such as N-methylmorpholine, pyridine or the like. The amount of the base is usually about 1 to 5 equivalents, preferably 1 to 3 equivalents, to the compound (IV).

Examples of the reactive derivatives of the compounds (VI) are the acid halide (e.g., chloride or bromide), acid anhydride, mixed acid anhydride (e.g., anhydride with methyl carbonate, anhydride with ethyl carbonate, anhydride with isobuthyl carbonate or the like), active ester (e.g., ester with hydroxy succinimide, ester with 1-hydroxybenzotriazole, ester with N-hydroxy-5-norbornene-2,3-dicarboxyimide, ester with p-nitrophenol, ester with 8-oxyquinoline or the like). Especially, the acid halide is more preferable.

The compound (IV) or its salt is usually reacted with the reactive derivative of the compound (VI) in a solvent (e.g., chloroform, dichloromethane, ethylether, tetrahydrofuran, dioxane, dimethoxyethane, ethyl acetate, benzene, toluene, pyridine, N,N-dimethylformamide or the like) at about $-10°$ C. to 120° C., preferably about 0° C. to 100° C., optionally in the presence of a base for accelerating the reaction. The reaction time is about 1 to 48 hours, preferably about 1 to 24 hours. The amount of the reactive derivative of the compound (VI) to be used is usually about 1 to 5 equivalents, preferably about 1 to 3 equivalents, to the compound (IV) or its salt. Examples of the bases to be used are alkylamines such as triethylamine, cyclic amines such as N-methylmorpholine or pyridine, alkali metal carbonate such as sodium carbonate or potassium carbonate, alkali metal hydrogen carbonate such as sodium hydrogen carbonate, or the like. The amount of the base is about 1 to 5 equivalents, preferably 1 to 3 equivalents, to the compound (IV) or its salt. In the case where a solvent immiscible with water is used, the reaction may be carried out by adding water in a two-layer system.

4) The compound (I) having an unsaturated alkylene group (e.g., $-CH=CH-$) as Z is, if necessary, reduced to convert to the compound (I) having the corresponding saturated alkylene group (e.g., $-CH_2CH_2-$) as Z.

Usable reducing agents are metal hydrides such as lithium aluminum hydride, sodium borohydride, lithium borohydride, and the like. The amount of the reducing agent is usually about 0.5 to 5 equivalents, preferably 0.5 to 2 equivalents, to the compound (I) in which Z is an unsaturated alkylene group. The reaction is usually carried out in a solvent (e.g., methanol, ethanol, ethyl ether, tetrahydrofuran, dioxane or the like) at about $-5°$ C. to 120° C., preferably 0° C. to 100° C. The reaction time is usually about 30 minutes to 12 hours, preferably about 30 minutes to 6 hours.

The reduction may be conducted by using a metal and an acid or a metal and a base, instead of using the aforesaid reducing agent. When a metal such as a zinc, tin, lead or the like is used, an acid (e.g., hydrochloric acid, sulfuric acid, acetic acid or the like) is mainly employed as a hydrogen supplying source, while a base (e.g., ammonia methylamine, dimethylamine, ethylamine, diethylamine or the like) is mainly employed as a hydrogen supplying source when a metal of potassium, sodium, lithium or the like is used. The amount of the metal to be used in the reduction is about 1 to 10 equivalents, preferably 1 to 5 equivalents to the compound (I) in which Z is an unsaturated alkylene group. The reduction is usually carried out in a solvent (e.g., alcohols such as methanol, ethanol or the like, or ethers such as tetrahydrofuran, dioxane, dimethoxyethane, or the like). The acid or base used for the reduction may be employed as a solvent. The temperature for reduction is about 0° C. to 120° C., preferably 0° C. to 80° C. The reaction time is about 30 minutes to 12 hours, preferably about 30 minutes to 6 hours.

The aforesaid reduction may be a catalytic reduction using a catalyst. Examples of the catalysts to be used are palladium black, palladium carbon, platinum oxide, platinum black, Raney nickel, carbon rhodium or the like. The catalytic reduction is usually carried out in a solvent (e.g., methanol, ethanol, isopropanol, tetrahydrofuran, dioxane, dimethoxyethane, formic acid, acetic acid, N,N-dimethylformamide or the like) under from atmospheric pressure to 20 atm., preferably from atmospheric pressure to 5 atm. The temperature for the catalytic reduction is about 0° C. to 100° C., preferably about 0° C. to 80° C. The reaction time is usually about 30 minutes to 24 hours, preferably about 30 minutes to 12 hours.

When the compound (I) prepared by the above method contains lower alkoxy group(s), such group(s), if required, can be converted into hydroxyl group(s) by the reaction with boron tribromide or the like. This reaction is usually carried out in a solvent (e.g., dichloromethane, chloroform, carbon tetrachloride, benzene, toluene, etc.), at about −20° C. to 80° C., preferably at about 0° C. to 30° C. The amount of boron tribromide to be used is about 1 to 10 equivalents, preferably about 1 to 5 equivalents, to each lower alkoxy group. The reaction time is usually about 15 minutes to 24 hours, preferably about 30 minutes to 12 hours.

The compound (I) which contains hydroxyl group(s) on its benzene ring can be converted, if required, into the corresponding one having alkoxy or acyloxy group(s) upon alkylation or acylation. The alkylation can be conducted by using an alkylating agent such as a halide (e.g., chloride, bromide or iodide), sulfuric acid ester or sulfonic acid ester (e.g., methanesulfonate, p-toluenesulfonate or benzenesulfonate) of an optionally substituted alkane in a solvent (e.g., methanol, ethanol, propanol, dimethoxyethane, dioxane, tetrahydrofuran, acetone, N,N-dimethylformamide or the like) in the presence of a base (e.g., organic bases such as trimethylamine, triethylamine, N-methylmorpholine, pyridine, picoline, N,N-dimethylaniline or the like, or inorganic bases such as potassium carbonate, sodium carbonate, potassium hydroxide, sodium hydroxide or the like). The reaction temperature may be usually about −10° C. to 100° C., preferably about 0° C. to 80° C. The amount of the alkylating agent is about 1–5 equivalents, preferably about 1 to 3 equivalents, to the phenolic derivative. The reaction time is usually about 15 minutes to 24 hours, preferably about 30 minutes to 12 hours.

The acylation can be conducted by using an appropriate carboxylic acid or its reactive derivative. The reaction varies with the kind of the reactive derivative or the kind of the phenolic derivative, but is usually conducted in a solvent (e.g., benzene, toluene, ethyl ether, ethyl acetate, chloroform, dichloromethane, dioxane, tetrahydrofuran, N,N-dimethylformamide or pyridine), optionally in the presence of an appropriate base for accelerating the reaction (e.g., sodium hydrogen carbonate, potassium hydrogen carbonate, sodium carbonate, potassium carbonate, sodium acetate, triethylamine or pyridine). The reactive derivative may be the acid anhydride, mixed acid anhydride or acid halide (e.g., chloride or bromide). The amount of the acylating agent to be used is about 1 to 5 equivalents, preferably about 1 to 3 equivalents, to the phenolic derivative. The reaction temperature is usually about 0° C. to 150° C., preferably about 10° C. to 100° C. The reaction time is usually about 15 minutes to 12 hours, preferably about 30 minutes to 6 hours.

When the compound (I) prepared by the above method contains an esterified carboxyl or acyloxy group, such group if required can be converted into a carboxyl or hydroxyl group, respectively, upon hydrolysis. The hydrolysis can usually be conducted by using an alkali metal or alkaline earth metal hydroxide such as sodium hydroxide, potassium hydroxide or barium hydroxide in the presence of a solvent (e.g., an alcohol such as methanol, ethanol or propanol, or an ether such as tetrahydrofuran, dioxane, dimethoxyethane), or mixtures thereof. The amount of hydroxide to be used is about 1 to 5 equivalents, preferably about 1 to 3 equivalents, to the compound (I). The reaction temperature is about 0° C to 100° C, preferably about 20° C. to 80° C. The reaction time is usually about 5 minutes to 12 hours, preferably about 15 minutes to 6 hours.

The object compounds (I) obtained in the above methods can be isolated and purified by a known method for isolation and purification (e.g., condensation, extraction by solvent, column chromatography, recrystallization, etc.).

When the object compounds (I) form solvates, they are also included in the scope of this invention.

The compounds (I) possess excellent inhibitory action against acyl-CoA: cholesterol acyltransferase (ACAT), and their acute toxicity and toxicity by repeated administration are low.

It is known that ACAT is an enzyme relating to the esterification of cholesterol with higher fatty acids in cells, and plays an important role in the absorption of cholesterol through the small intestine and accumulation of cholesterol ester in the cells. Accordingly, ACAT inhibitors can inhibit the absorption of dietary cholesterol through the intestinal tract, restrain the rise of blood cholesterol level, restrain the accumulation of cholesterol ester in the cells at the atherosclerotic lesion and therefore prevent the progress of atherosclerosis.

The compounds (I) of the present invention are useful as a safe drug for preventing and treating hypercholesterolemia, atherosclerosis and diseases caused thereby (e.g., ischemic cardiac diseases such as myocardial infarction, cerebrovascular disturbances such as cerebral infarction, cerebral apoplexy, etc.) in mammals (e.g., mouse, rat, hamster, rabbit, cat, dog, horse, cattle, sheep, monkey, human, etc.).

Some of the compounds (I) exhibit inhibitory action against lipid peroxidation (antioxidizing action). It is known that lipid peroxidation in the organism or low density lipoprotein (LOL) is strongly related to arteriosclerosis and ischemic cardiac diseases in the brain or cardiovascular system. Accordingly, the compounds (I) having both ACAT inhibitory action and antioxidizing action are highly useful in preventing and treating various diseases in cardiovascular or cerebrovascular system caused by high blood cholesterol level and lipid peroxidation.

The compounds (I), when used as a drug, are mixed with a pharmaceutically acceptable carrier, diluent or excipient to form powders, granules, tablets, capsules or injections for oral preparations or parenteral preparations. The compound (I) is preferably administered orally when it is used for the purpose of inhibiting the absorption of cholesterol. Dosage of the compound (I) depends on the kind of the compound, administration route, condition and age of the patient, etc. For example, when a compound (I) is administered orally to an adult patient having hypercholesterolemia, a daily dose of about 0.005–50 mg, preferably about 0.05–10 mg, more preferably about 0.2–4 mg of the compound is administered per 1 kg of weight of the patient, preferably divided into 1–3 times.

The compounds (II) or (IV) as the starting materials for the compounds (I) can be prepared by methods known in the art but may be industrially advantageously prepared e.g., by the following method.

[Method A]

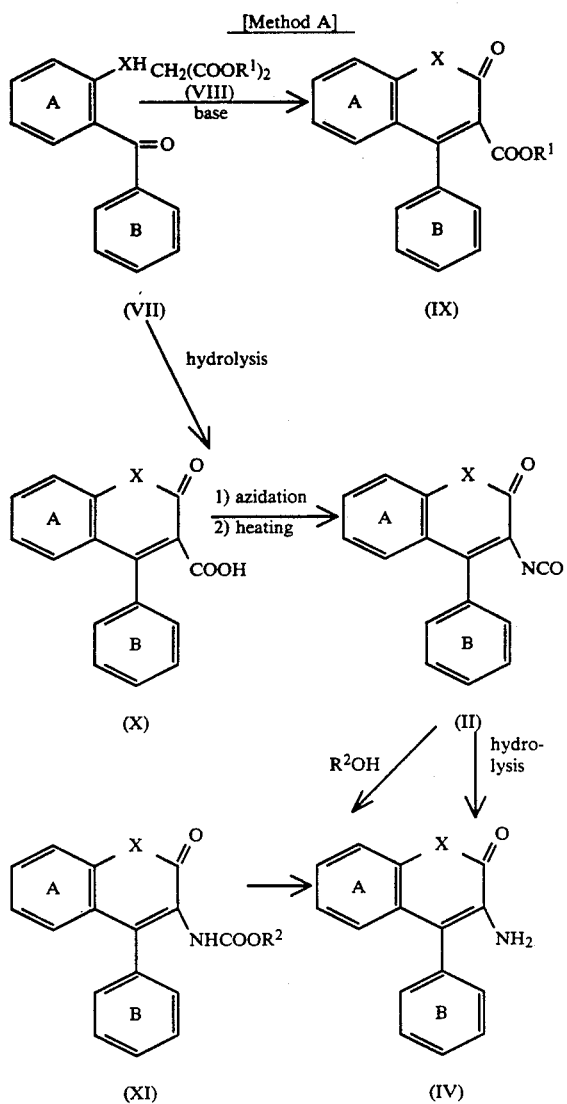

In the above formulas, each of $R^1$ and $R^2$ is a $C_{1-6}$ alkyl group (e.g., methyl, ethyl, propyl, isopropyl, butyl, tert-butyl, pentyl, hexyl, cyclohexyl or the like) and other symbols have the same meanings as defined above.

The compound (IX) can be prepared by reacting a 2-hydroxy or 2-mercaptobenzophenone derivative (VII) with a malonic acid diester (VIII) in this method.

The reaction is usually conducted under heating without any solvent, preferably in the presence of an amine [e.g., piperidine, pyrrolidine, triethylamine, 1,5-diazabicyclo[4.3.0]non-5-ene(DBN), 1,8-diazabicyclo[5.4.0]-7-undecene(DBU) or 1,4-diazabicyclo[2.2.2]octane(DABCO)], potassium fluoride, cesium fluoride or the like. The reaction temperature is usually about 60° C. to 220° C., preferably about 80° C. to 200° C. The reaction time is usually about 1 to 60 hours, preferably about 1 hour to 24 hours. The amount of the catalysts to be used is about 0.01 to 2 equivalents, preferably 0.05 to 1 equivalents, to the compound (VII). The reaction may be carried out, if required, in a solvent such as aromatic hydrocarbons (e.g., toluene, xylene, chlorobenzene, nitrobenzene, diphenyl ether or biphenyl).

Next, the compound (IX) is hydrolyzed to give the carboxylic acid (X), which then is subjected to azidation followed by heating to convert into the 3-isocyanate derivative (II).

The hydrolysis of the compound (IX) can be usually conducted by using an alkali metal or alkaline earth metal hydroxide (e.g., sodium hydroxide, potassium hydroxide or barium hydroxide) in a solvent (e.g., alcohols such as methanol, ethanol and propanol, or ethers such as dioxane, tetrahydrofuran or dimethoxyethane). The reaction temperature is about 0° C. to 120° C., preferably about 20° C. to 100° C. The reaction time is usually about 30 minutes to 12 hours, preferably about 1 hour to 6 hours. The alkali is used in an amount of about 1 to 10 equivalents, preferably about 1 to 5 equivalents, to the compound (IX). The hydrolysis reaction may be conducted in the presence of an acid. Examples of the acids are mineral acids (e.g., hydrochloric acid, sulfuric acid, phosphoric acid or hydrobromic acid), organic acids (e.g., formic acid, acetic acid, propionic acid, p-toluensulfonic acid or trifluoroacetic acid) or mixtures thereof. The hydrolysis reaction may be carried out in a solvent, e.g., alcohols such as methanol, ethanol, propanol or isopropanol, or ethers such as dioxane, tetrahydrofuran, methoxyethanol or dimethoxyethanol. The reaction temperature is about 60° C. to 180° C., preferably about 80° C. to 150° C. The reaction time is usually about 1 hour to 60 hours, preferably 1 hour to 24 hours.

Any known methods for converting a carboxylic acid to an acid azide can be applied for the compound (X). For example, the compound (X) can be converted to the corresponding acid azide by using diphenylphosphoryl azide (DPPA) as an azidating agent. This reaction can be usually carried out in an inert solvent (e.g., ethers such as ethyl ether, isopropyl ether, dimethoxyethane, tetrahydrofuran or dioxane; aromatic hydrocarbons such as benzene, toluene or xylene; esters such as methyl acetate or ethyl acetate, ketones such as acetone or 2-butanone; pyridine or N,N-dimethylformamide). The reaction may be conducted in the presence of a base (e.g., trimethylamine, triethylamine or N-methylmorpholine). The reaction is usually carried out at about 0° C. to 120° C., preferably at about 10° C. to 100° C. The reaction time is usually about 5 minutes to 12 hours, preferably about 10 minutes to 6 hours. The amount of DPPA to be used is usually about 1 to 2 equivalents, preferably about 1 to 1.5 equivalents, to the compound (X).

The thus produced acid azide is usually converted to the isocyanate (II) without isolation by heating, although the acid azide can be isolated and purified by a conventional method. This conversion reaction is preferably carried out in a solvent used for the azidation. The conversion reaction is carried out under heating usually at about 30° C. to 200° C., preferably at about 30° C. to 150° C. The reaction time is about 5 minutes to 6 hours, preferably about 5 minutes to 3 hours. The produced compound (II) can be isolated by a known method or used as the starting material for preparing the 3-amino compound (IV) or urethane compound (XI).

That is, the compound (II) can be converted into the 3-amino compound (IV) upon hydrolysis. The hydrolysis is conducted under the same conditions as in the hydrolysis reaction from the compound (IX) to the compound (X).

The compound (XI) can be prepared by reacting the compound (II) with an alcohol such as methanol, ethanol, propanol or tert-butanol. The reaction is usually conducted in a solvent of desired alcohol. However, the reaction may be carried out in a solvent in which the alcohol is mixed with an ether such as tetrahydrofuran, dioxane or dimethoxyethane, an aromatic hydrocarbon such as benzene, toluene or xylene, N,N-dimethylformamide or pyridine. The reaction temperature is usually about 0° C. to 150° C., preferably about 10° C. to 120° C., and the reaction time is about 5 minutes to 12 hours, preferably about 15 minutes to 10 hours.

Further, the 3-amino compound (IV) can be prepared from the compound (XI) under the same condition as in the method for preparing the compound (X) from the compound (IX).

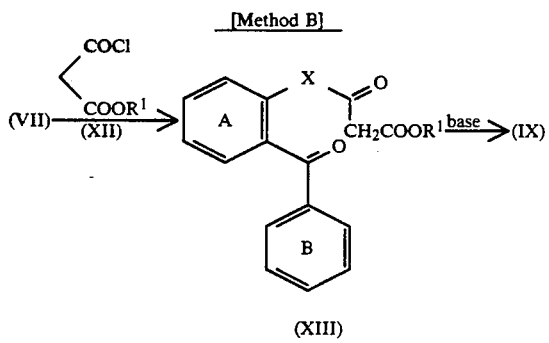

(XIII)

In this method, the compound (XIII) is prepared by reacting the compound (VII) with the compound (XII). The reaction is usually carried out in a solvent (e.g., halogenated hydrocarbons such as dichloromethane or chloroform, esters such as methyl acetate or ethyl acetate, ethers such as ethyl ether, tetrahydrofuran, dioxane or dimethoxyethane, aromatic hydrocarbons such as benzene or toluene or amides such as dimethylformamide) in the presence of a base (e.g., trimethylamine, triethylamine, DBU, DBN, potassium carbonate or sodium carbonate). The reaction temperature is usually about −10° C. to 150° C., preferably about −5° C. to 80° C. The reaction time is usually about 5 minutes to 10 hours, preferably about 10 minutes to 5 hours. Each amount of the compound (XII) and base is about 1 to 10 equivalents, preferably about 1 to 5 equivalents to the compound (VII).

Next, the compound (IX) is prepared from the compound (XIII) by the ring-closure reaction. The reaction is usually carried out in a solvent such as alcohols (e.g., methanol, ethanol, propanol or tert-butanol), aromatic hydrocarbons (e.g., benzene, toluene or xylene) or ethers (e.g., ethyl ether, tetrahydrofuran, dioxane, or dimethoxyethane) in the presence of a base. The reaction may be conducted without solvent. Usable bases are those used for preparing the compound (XI) from the compound (VII) in Method A. The reaction temperature is usually about 0° C. to 220° C., preferably about 20° C. to 180° C. The reaction time is usually about 15 minutes to 20 hours, preferably about 30 minutes to 10 hours. The amount of the base is about 0.01 to 5 equivalents, preferably about 0.05 to 3 equivalents to 1 mol of the compound (XIII).

The thus produced compounds (II), (IV) or (IX) can be isolated and purified by a known method for isolation and purification, or can be used as starting materials without isolation for next procedures.

Activity

Pharmacological test results on the compounds (I) and their salts of the present invention are shown in the following.

1. Acyl-CoA : cholesterol acyltransferase (ACAT) inhibitory activity

Methods

The enzyme ACAT was prepared by the method of Heider et al. described in Journal of Lipid Research, Vol. 24, page 1127 (1982), from the mucosal microsome fraction of the small intestine of male, 6-week old Sprague-Dawley rats which had been fasted for 20 hours.

ACAT activity was calculated by the method of Helgerud et al. described in Journal of Lipid Research, Vol. 22, page 271 (1981), namely, by measuring the amount of the labeled cholesterol ester produced from $[1^{14}C]$ oleoyl-CoA and endogenous cholesterol.

Results

Inhibition rates (%) of the production of the labeled cholesterol ester wherein $10^{-6}M$ or $10^{-8}M$ of test compounds were added are shown as an index of ACAT inhibitory activity in Table 1.

TABLE 1

| Test Compound (Example No.) | ACAT Inhibition Rate (%) | |
|---|---|---|
| | $10^{-6}M$ | $10^{-8}M$ |
| 1 | 99.0 | — |
| 2 | 99.0 | — |
| 3 | 99.2 | — |
| 4 | — | 69.7 |
| 6 | — | 45.9 |
| 7 | — | 81.7 |
| 11 | — | 86.7 |
| 16 | — | 42.7 |
| 17 | — | 84.2 |
| 18 | — | 56.1 |
| 19 | 92.3 | — |
| 20 | 84.8 | — |
| 22 | 97.0 | — |
| 24 | 98.6 | — |
| 25 | 98.8 | — |
| 26 | 98.5 | — |
| 27 | 99.1 | — |
| 28 | — | 34.3 |
| 29 | 95.4 | — |
| 30 | 90.2 | — |

Table 1 shows that the object compounds of the present invention possess excellent inhibitory action against acyl-CoA : cholesterol acyltransferase (ACAT).

EXAMPLE 1

Triethylamine (0.14ml) was dropwise added to a mixture of 6-chloro-4-(2-methylphenyl)-2-oxo-2H-1-benzopyran-3-carboxylic acid (342 mg), diphenylphosphoryl azide (DPPA, 330 mg) and benzene (5 ml) under stirring. The mixture was stirred for 20 minutes at room temperature and for 20 minutes under reflux, to which 2,4-difluoroaniline (0.12 ml) was added and further stirred for 2 hours at room temperature. The reaction mixture to which water was added was extracted with ethyl acetate. The extract was washed with water, a saturated NaHCO₃ aqueous solution and water, and then dried (MgSO₄). The solvent was distilled off to obtain crystals of N-[6-chloro-4-(2-methylphenyl)-2-oxo-2H-1-benzopyran-3-yl]-N'-(2,4-difluorophenyl)

urea (311 mg, 70.7%). Recrystallization from ethanol gave colorless needles of mp 210–212° C.
Elemental analysis for $C_{23}H_{15}ClF_2N_2O_3$:
Calculated: C 62.67; H 3.43; N 6.35.
Found : C 62.66; H 3.39; N 6.30.

EXAMPLE 2

By the same method as in Example 1, N-(2,4-difluorophenyl)-N'-[6-isopropyl-4-(2-methylphenyl)-2-oxo-2H-1-benzopyran-3-yl] urea was obtained as colorless prisms.
Yield: 64.3%
mp: 199–200° C. (recrystallized from ethanol)
Elemental analysis for $C_{26}H_{22}F_2N_2O_3$:
Calculated : C 69.63; H 4.94; N 6.25.
Found : C 69.47; H 5.02; N 6.20.

EXAMPLE 3

By the same method as in Example 1, N-(2,4-difluorophenyl)-N'-[4-(2-methylphenyl)-6,7-dimethyl-2-oxo-2H-1-benzopyran-3-yl] urea was obtained as colorless needles.
Yield: 82.5%
mp: 215–217° C. (from ethanol)
Elemental analysis for $C_{25}H_{20}F_2N_2O_3$:
Calculated : C 69.12; H 4.64; N 6.45.
Found : C 69.10; H 4.74; N 6.35.

EXAMPLE 4

To a solution of 3-amino-6,7-dimethyl-4-(2-methylphenyl)-2H-1-benzopyran-2- one (279 mg) in tetrahydrofuran (4 ml) was added 4-chlorophenylisocyanate (184 mg). The mixture was stirred for 3 days at room temperature and distilled to remove the solvent. Ethyl ether was added to the residue to obtain crystals of N-(4-chlorophenyl)-N'-[6,7-dimethyl-4-(2-methylphenyl)-2-oxo-2-H-1-benzopyran-3-yl] urea (382 mg, 88.2%). Recrystallization from acetone gave colorless needles.
mp: 234–236° C.
Elemental analysis for $C_{25}H_{21}ClN_2O_3$:
Calculated: C 69.36; H 4.89; N 6.47.
Found: C 69.18; H 4.98; N 6.55.

EXAMPLE 5

To a mixture of 6-chloro-2-oxo-4-phenyl-2H-1-benzopyran-3-carboxylic acid (300 mg), DPPA (330 mg) and benzene (5 ml) was dropwise added triethylamine (0.14 ml) under stirring. The mixture was stirred for 30 minutes at room temperature and for 30 minutes under reflux, to which 2,4-difluoroaniline (0.12 ml) was added and refluxed. After adding water, the mixture was extracted with ethyl acetate. The extract was washed with water, a saturated $NaHCO_3$ aqueous solution and then water, dried and distilled to remove the solvent. Isopropyl ether was added to the residue to obtain crystals of N-(6-chloro-4-phenyl-2-oxo-2 H-1-benzopyran-3-yl)-N'-(2,4-difuorophenyl) urea (347 mg, 81.5%). Recrystallization from ethanol gave colorless needles.
mp: 209–210° C.
Elemental analysis for $C_{22}H_{13}ClF_2N_2O_3$:
Calculated: C 61.91; H 3.07; N 6.56.
Found: C 61.88; H 2.96; N 6.50.

EXAMPLE 6

By the same method as in Example 5, N-[6-ethyl-4-(2-methylphenyl)-2-oxo-2H-1-benzopyran-3-yl]-N'-(2,4-difluorophenyl) urea was obtained as colorless needles.
Yield: 73.7%
mp: 210–211° C. (from ethanol)
Elemental analysis for $C_{25}H_{20}F_2N_2O_3$:
Calculated: C 69.12; H 4.64; N 6.45.
Found: C 69.24; H 4.60; N 6.41.

EXAMPLE 7

By the same method as in Example 5, N-[6-chloro-7-methyl-4-(2-methylphenyl)-2-oxo-2H-1-benzopyran-3-yl)-N'-(2,4-difluorophenyl) urea was obtained as colorless needles.
Yield: 88.8%
mp: 224–225° C. (from ethanol)
Elemental analysis for $C_{24}H_{17}ClF_2N_2O_3$:
Calculated : C 63.74; H 3.77; N 6.16.
Found : C 63.70; H 3.75; N 6.12.

EXAMPLE 8

By the same method as in Example 5, N-[6-chloro-4-(2-methylphenyl)-2-oxo-2H-1-benzopyran-3-yl)-N'-(2-isopropyl-6-methylphenyl) urea was obtained as colorless needles.
Yield: 88.9%
mp: 237–238° C. (from ethanol)
Elemental analysis for $C_{27}H_{25}ClN_2O_3$:
Calculated: C 70.35; H 5.47; N 6.08.
Found: C 70.48; H 5.47; N 6.21.

EXAMPLE 9

By the same method as in Example 5, N-[5,6-dimethyl-4-(2-methylphenyl)-2-oxo-2H-1-benzopyran-3-yl)-N'-(2,4-difluorophenyl) urea was obtained as colorless needles.
Yield: 71.0%
mp: 232–234° C. (from acetone)
Elemental analysis for $C_{25}H_{20}F_2N_2O_3$:
Calculated: C 69.12; H 4.64; N 6.45.
Found: C 69.50; H 4.73; N 6.47.

EXAMPLE 10

By the same method as in Example 5, N-[6-chloro-4-(3,4-dimethoxyphenyl)-2-oxo-2H-1-benzopyran-3-yl)-N'-(2,4-difluorophenyl) urea was obtained as colorless needles.
Yield: 48.3%
mp: 267–270° C. (from acetone)
Elemental analysis for $C_{24}H_{17}ClF_2N_2O_5$:
Calculated: C 59.21; H 3.52; N 5.75.
Found: C 59.14; H 3.58; N 5.71.

EXAMPLE 11

By the same method as in Example 5, N-[4-(2-chlorophenyl-6,7-dimethyl-2-oxo-2H-1-benzopyran-3-yl-N'-(2,4-difluorophenyl) urea was obtained as colorless prisms.
Yield: 91.0%
mp: 212–214° C. (from acetone-hexane)
Elemental analysis for $C_{24}H_{17}ClF_2N_2O_3$:
Calculated: C 63.37; H 3.77; N 6.16.
Found: C 63.64; H 3.70; N 6.15.

EXAMPLE 12

By the same method as in Example 5, N-[6,8-difluoro-4-(2-methylphenyl)-2-oxo-2H-1-benzopyran- 3-yl)-N'-(2,6-dimethylphenyl) urea was obtained as colorless crystals.
Yield: 84.1%
mp: 221–222° C. (from acetone)

Elemental analysis for $C_{25}H_{20}F_2N_2O_3$:
Calculated: C 69.12; H 4.64; N 6.45.
Found: C 69.02; H 4.55; N 6.30.

EXAMPLE 13

By the same method as in Example 5, N-[6,8-difluoro-4-(2-methylphenyl)-2-oxo-2H-1-benzopyran-3-yl]-N'-(2,4-difluorophenyl) urea was obtained as colorless needles.
Yield: 81.9%
mp: 220–221° C. (from ethanol)
Elemental analysis for $C_{23}H_{14}F_4N_2O_3$:
Calculated: C 62.45; H 3.19; N 6.33.
Found: C 62.47; H 3.11; N 6.36.

EXAMPLE 14

By the same method as in Example 5, N-[6,8-difluoro-4-(2-methylphenyl)-2-oxo-2H-1-benzopyran-3-yl]-N'-(2-isopropyl-6-methylphenyl) urea was obtained as colorless needles.
Yield: 80.5%
mp: 219–220° C. (from acetone)
Elemental analysis for $C_{27}H_{24}F_2N_2O_3$:
Calculated: C 70.12; H 5.23; N 6.06.
Found: C 70.17; H 5.26; N 6.06.

EXAMPLE 15

By the same method as in Example 5, N-[6-chloro-4-(2-fluorophenyl)-2-oxo-2H-1-benzopyran-3-yl]-N'-(2-isopropyl-6-methylphenyl) urea was obtained as colorless prisms.
Yield: 80.7%
mp: 217–218° C. (from acetone-hexane)
Elemental analysis for $C_{26}H_{22}ClFN_2O_3 \cdot \frac{1}{8}(CH_3)_2CO$:
Calculated: C 67.04; H 5.00; N 5.79.
Found: C 67.25; H 4.90; N 5.85.

EXAMPLE 16

By the same method as in Example 5, N-[2,4-difluorophenyl]-N'-[6-methyl-4-(2-methylphenyl)-2-oxo-2H-1-benzopyran-3-yl] urea was obtained as colorless prisms.
Yield 86.2%
mp: 213–214° C. (from acetone-hexane)
Elemental analysis for $C_{24}H_{18}F_2N_2O_3$:
Calculated: C 68.57; H 4.32; N 6.66.
Found: C 68.44; H 4.36; N 6.56.

EXAMPLE 17

By the same method as in Example 5, N-[7-chloro-6-methyl-4-(2-methylphenyl)-3-oxo-2H-1-benzopyran-3-yl]-N'-(2,4-difluorophenyl) urea was obtained as colorless needles.
Yield: 84.8%
mp: 233–234° C. (from acetone)
Elemental analysis for $C_{24}H_{17}ClF_2N_2O_3$:
Calculated: C 63.37; H 3.77; N 6.16.
Found: C 63.54; H 3.62; N 6.15.

EXAMPLE 18

By the same method as in Example 5, N-[4-(2-chlorophenyl)-6-methyl-2-oxo-2H-1-benzopyran-3-yl]-N'-(2,4-difluorophenyl) urea was obtained as colorless prisms.
Yield: 89.1%
mp: 214–215° C. (from acetone-hexane)
Elemental analysis for $C_{23}H_{15}ClF_2N_2O_3$:
Calculated: C 62.67; H 3.43; N 6.35.
Found: C 62.84; H 3.44; N 6.30.

EXAMPLE 19

To a mixture of 4-acetoxy-3,5-dimethoxycinnamic acid (640 mg), dimethylformamide (2 drops) and tetrahydrofuran (8 ml) was dropwise added oxalyl chloride (0.26 ml). The mixture was stirred for 30 minutes at room temperature and distilled to remove the solvent. A solution of the residue in dichloromethane (5 ml) was dropwise added to a mixture of 3-amino-6-chloro-7-methyl-4-(2-methylphenyl)-2H-1-benzopyran-2-one (600 mg), triethylamine (0.34 ml) and dichloromethane (10 ml) under ice-cooling. The mixture was stirred for 30 hours at room temperature, washed with water, dried (MgSO4) and then distilled to remove the solvent. The residue was treated with ethyl acetate-ethyl ether to obtain crystals (315 mg, 28.8%). The crystals were recrystallized from acetone to obtain pale-yellowish prisms of 3-(4-acetoxy-3,5-dimethoxycinnamoylamino)-6-chloro-7-methyl-4-(2-methylphenyl)-2H-1-benzopyran-2-one.
mp: 248–250° C.
Elemental analysis for $C_{30}H_{26}ClNO_7$:
Calculated: C 65.75; H 4.78; N 2.56.
Found: C 65.72; H 4.80; N 2.57.

EXAMPLE 20

A mixture of 3-amino-6-chloro-7-methyl-4-(2-methylphenyl)-2H-benzopyran-2-one (297 mg), 3-trifluoromethylphenylisocyanate (374 mg) and benzene (4 ml) was refluxed for 2 hours and then distilled to remove the solvent. The residue was crystallized from ethyl ether. The resulting crystals were recrystallized from ethanol to obtain colorless needles of N-[6-chloro-7-methyl-4-(2-methylphenyl)-2-oxo-2H-1-benzopyran-3-yl]-N'-(3-trifluoromethylphenyl) urea.
mp: 203–205° C.
Elemental analysis for $C_{25}H_{18}ClF_3N_2O_3$:
Calculated: C 61.67; H 3.73; N 5.75.
Found: C 61.68; H 3.69; N 5.64.

EXAMPLE 21

By the same method as in Example 20, N-(6,8-dimethyl-2 2-oxo-4-phenyl-2H-1-benzopyran-3-yl)-N'-(3-trifluoromethy-1-phenyl) urea was obtained as colorless needles.
Yield: 53.4%
mp: 245–246° C. (from acetone)
Elemental analysis for $C_{25}H_{19}F_3N_2O_3$:
Calculated: C 66.37; H 4.23; N 6.19.
Found: C 66.33; H 4.15; N 6.17.

EXAMPLE 22

By the same method as in Example 5, N-[6-chloro-7-methyl-4-(2-methylphenyl)-2-oxo-2H-1-thiobenzopyran-3-y-1)-N'-(2,4-difluorophenyl) urea was obtained as colorless needles.
Yield: 73.6%
mp: 206–208° C. (from acetone-hexane)
Elemental analysis for $C_{24}H_{17}ClF_2N_2O_2S$:
Calculated: C 61.21; H 3.64; N 5.95.
Found: C 61.21; H 3.64; N 5.91.

EXAMPLE 23

By the same method as in Example 19, 3-(4-acetoxy-3,5-dimethoxycinnamoylamino)-6,8-dimethyl-4-phenyl-2H-1-benzopyran-2-one was obtained as colorless needles.
Yield: 89.9% mp: 245–248° C. (from acetone-hexane)
Elemental analysis for $C_{30}H_{27}NO_3$:
Calculated: C 70.16; H 5.30; N 2.73.
Found: C 69.82; H 5.36; N 2.62.

EXAMPLE 24

By the same method as in Example 5, ½ acetone solvate of N-(4-acetoxy-3,5-dimethoxyphenyl)-N'-[4-(2-chlorophenyl)-6-methyl-2-oxo-2H-1-benzopyran-3-yl] urea was obtained as colorless needles.
Yield: 73.4%
mp: 238–240° C. (from acetone)
Elemental analysis for $C_{27}H_{23}ClN_2O_7 \cdot \frac{1}{2}(CH_3)_2CO$:
Calculated: C 62.02; H 4.75; N 5.08.
Found: C 62.17; H 4.78; N 5.04.

EXAMPLE 25

By the same method as in Example 5, N-(4-acetoxy-3,5-dimethoxyphenyl)-N'-[6,7-dimethyl-4-(2-methylphenyl)-2-oxo-2H-1-benzopyran-3-yl]urea was obtained as colorless needles.
Yield: 85.9%
mp: 238–240° C. (from acetone-hexane)
Elemental analysis for $C_{29}H_{28}N_2O_7$:
Calculated: C 67.43; H 5.46; N 5.42.
Found: C 67.34; H 5.41; N 5.42.

EXAMPLE 26

By the same method as in Example 5, N-(4-acetoxy-3,5-dimethoxyphenyl)-N,-[6-chloro-7-methyl-4-(2-methylphenyl)-2-oxo-2H-1-benzopyran-3-yl]urea was obtained as colorless needles.
Yield: 84.1%
mp: 240–242° C. (from acetone-hexane)
Elemental analysis for $C_{28}H_{25}ClN_2O_7$:
Calculated: C 62.63; H 4.69; N 5.22.
Found: C 62.42; H 4.70; N 5.13.

EXAMPLE 27

By the same method as in Example 5, N-(4-acetoxy-3,5-dimethylphenyl)-N'-[6-chloro-7-methyl-4-(2-methylphenyl)-2-oxo-2H-1-benzopyran-3-yl]urea was obtained as colorless needles.
Yield: 58.7%
mp: 240–242° C. (from ethanol-chloroform)
Elemental analysis for $C_{28}H_{25}ClN_2O_5$:
Calculated: C 66.60; H 4.99; N 5.55
Found: C 66.78; H 5.10; N 5.55.

EXAMPLE 28

To a mixture of 2,4-difluorophenylacetic acid (206 mg), dimethylformamide (one drop) and tetrahydrofuran (4 ml) was dropwise added oxalyl chloride (0.13 ml). The mixture was stirred for an hour at room temperature and distilled to remove the solvent. The residue was dissolved in dichloromethane (5 ml), to which a mixture of 3-amino-6-chloro-7-methyl-4-(2-methylphenyl)-2H-1-benzopyran-2-one (300 mg), N,N-dimethylaniline (0.13 ml) and dichloromethane (5 ml) was dropwise added. The mixture was stirred for 15 hours at room temperature, washed with water, a saturated $NaHCO_3$ aqueous solution and then water, dried ($MgSO_4$) and distilled to remove the solvent. The residue was subjected to silica gel chromatography, eluting with hexane-ethyl acetate (3:1). By distilling off the solvent, 6-chloro-3-(2,4-difluorophenylacetylamino)-7-methyl-4-(2-methylphenyl)-2H-1-benzopyran-2-one was obtained as crystals (256 mg, 56.5%). Recrystallization from ethanol gave colorless needles.
mp: 159–160° C.
Elemental analysis for $C_{25}H_{18}ClF_2NO_3$:
Calculated: C 66.16; H 4.00; N 3.09.
Found: C 66.09; H 4.14; N 3.12.

EXAMPLE 29

To a mixture of 3-amino-6-chloro-7-methyl-4-(2-methylphenyl)-2H-1-benzopyran-2- one (300 mg), N,N-dimethylaniline (0.13 ml) and dichloromethane (4 ml) was dropwise added 2,4-difluorobenzoyl chloride (0.15 ml). The mixture was stirred for 20 hours at room temperature, washed with water and dried ($MgSO_4$). By distilling off the solvent, 6-chloro-3-(2,4-difluorobenzoylamino)-7-methyl-4-(2-methylphenyl)-2H-1-benzopyran-2-one was obtained as crystals (406 mg, 92.5%). Recrystallization from ethanol gave colorless prisms.
mp: 195–196° C.
Elemental analysis for $C_{24}H_{16}ClF_2NO_3$:
Calculated: C 65.54; H 3.67; N 3.18.
Found: C 65.32; H 3.62; N 3.10.

EXAMPLE 30

By the same method as in Example 5, N-(2,4-difluorophenyl)-N'-[4-(4-fluorophenyl)-6-isopropyl-2-oxo-2H-1-benzopyran-3-yl] urea was obtained as colorless crystals.
Yield: 79.0%
mp: 216–217° C. (from ethyl acetate-isopropyl ether)
Elemental analysis for $C_{25}H_{19}F_3N_2O_3$:
Calculated: C 66.37; H 4.23; N 6.19.
Found: C 66.48; H 4.31; N 6.01.

EXAMPLE 31

By the same method as in Example 5, N-[4-(3,5-di-tert-butyl-4-hydroxyphenyl)-6-chloro-2-oxo-2H-1-benzopyran-3-yl]-N'-(2,4-difluorophenyl) urea was obtained as colorless needles.
Yield: 36.9%
mp: 244–246° C. (from acetone)
Elemental analysis for $C_{30}H_{29}ClF_2N_2O_4$:
Calculated: C 64.92; H 5.27; N 5.05.
Found: C 64.92; H 5.11; N 5.06.

REFERENCE EXAMPLE 1

A mixture of 5-chloro-2-hydroxy-2'-methylbenzophenone (4.92 g), diethyl malonate (4.80 g) and 1,8-diazabicyclo [5,4,0]-7-undecene(DBU, 0.6 ml) was heated for 2 hours at 160° C. to 170° C. After cooling, the reaction mixture was subjected to silica gel chromatography, eluting with hexane-ethyl acetate (4:1), thereby affording ethyl 6-chloro-4-(2-methylphenyl)-2-oxo-2H-1-benzopyran-3-carboxylate as crystals (4.0 g, 58.5%). Recrystallization from ethanol gave colorless prisms.
mp: 97 98° C.
Elemental analysis for $C_{19}H_{15}ClO_4$:
Calculated: C 66.58; H 4.41.
Found: C 66.61; H 4.46.

The compounds in Table 2 were obtained by the same method as in Reference Example 1.

TABLE 2

| Structure | Chemical name | mp (°C.) |
|---|---|---|
| 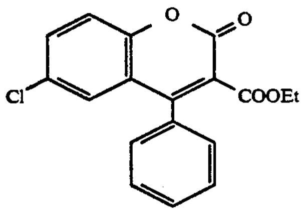 | ethyl 6-chloro-4-phenyl-2-oxo-2H-1-benzopyran-3-carboxylate | 108–109 |
| 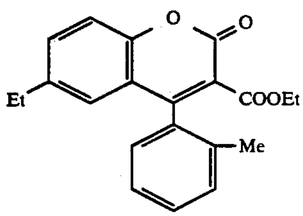 | ethyl 6-ethyl-4-(2-methyl-phenyl)-2-oxo-2H-1-benzo-pyran-3-carboxylate | 93–94 |
| 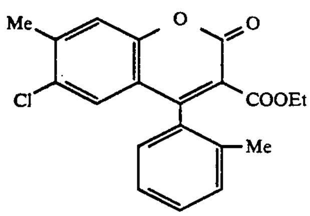 | ethyl 6-chloro-7-methyl-4-(2-methylphenyl)-2-oxo-2H-1-benzopyran-3-carboxylate | 100–101 |
| 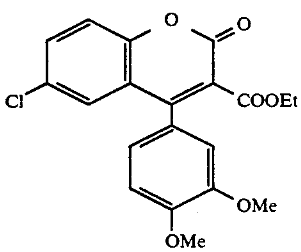 | ethyl 6-chloro-4-(3,4-dimethoxyphenyl)-2-oxo-2H-1-benzopyran-3-carboxylate | 138–139 |
| 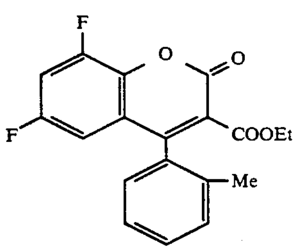 | ethyl 6,8-difluoro-4-(2-methylphenyl)-2-oxo-2H-1-benzopyran-3-carboxylate | 96–97 |
| 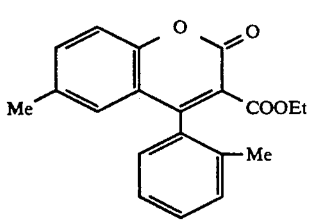 | ethyl 6-methyl-4-(2-methylphenyl)-2-oxo-2H-1-benzopyran-3-carboxylate | 99–100 |
| 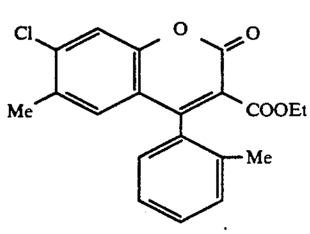 | ethyl 7-chloro-6-methyl-4-(2-methylphenyl)-2-oxo-2H-1-benzopyran-3-carboxylate | 122–123 |

TABLE 2-continued

| Structure | Chemical name | mp (°C.) |
|---|---|---|
| 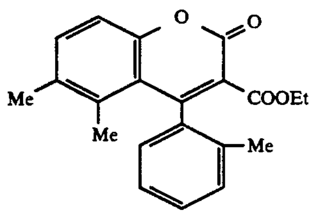 | ethyl 4-(2-methylphenyl)-5,6-dimethyl-2-oxo-2H-1-benzopyran-3-carboxylate | 130–131 |
| 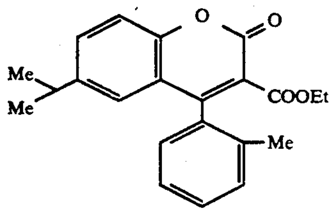 | ethyl 6-isopropyl-4-(2-methylphenyl)-2-oxo-2H-1-benzopyran-3-carboxylate | 85–86 |
| 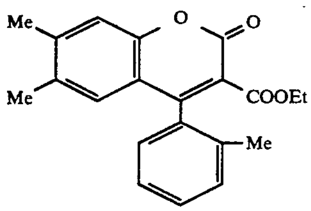 | ethyl 6,7-dimethyl-4-(2-methylphenyl)-2-oxo-2H-1-benzopyran-3-carboxylate | 94–95 |
| 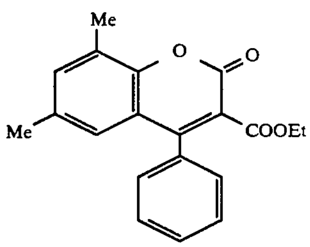 | ethyl 6,8-dimethyl-2-oxo-4-phenyl-2H-1-benzopyran-3-carboxylate | 152–153 |
| 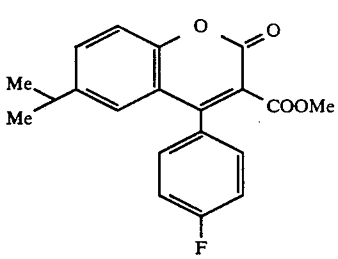 | methyl 4-(4-fluorophenyl)-6-isopropyl-2-oxo-2H-1-benzopyran-3-carboxylate | 163–164 |
| 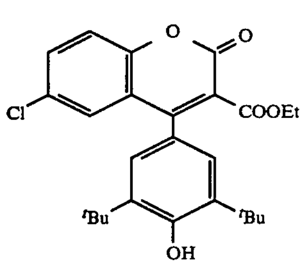 | ethyl 6-chloro-4-(3,5-di-tert-butyl-4-hydroxy-phenyl)-2-oxo-2H-1-benzopyran-3-carboxylate | 195–196 |

REFERENCE EXAMPLE 2

A mixture of ethyl 6-chloro-4-(2-methylphenyl)-2-oxo-2H-1-benzopyran-3-carboxylate (3.0 g), 6N-HCl (10 ml) and acetic acid (15 ml) was refluxed for 10 hours. Water was added to the reaction mixture, by which 6-chloro-4-(2-methylphenyl)-2-oxo-2H- 1-benzopyrancarboxylic acid (2.58 g, 93.8%) was obtained. Recrystallization from ethyl acetate gave colorless plates.

mp: 220–221° C.
Elemental analysis for $C_{17}H_{11}ClO_4$:
Calculated: C 64.88; H 3.52.
Found: C 65.01; H 3.54.

Compounds in Table 3 were obtained by the same method as in Reference Example 2.

TABLE 3

| Structure | Chemical name | mp (°C.) |
|---|---|---|
| 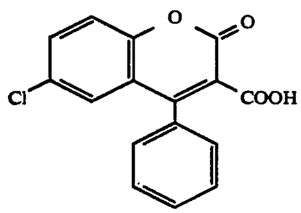 | 6-chloro-4-phenyl-2-oxo-2H-1-benzopyran-3-carboxylic acid | 180–181 |
| 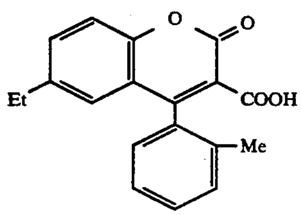 | 6-ethyl-4-(2-methylphenyl)-2-oxo-2H-1-benzopyran-3-carboxylic acid | 167–168 |
| 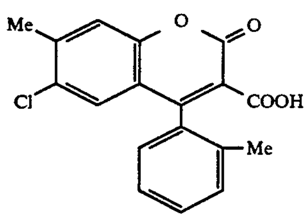 | 6-chloro-7-methyl-4-(2-methylphenyl)-2-oxo-2H-1-benzopyran-3-carboxylic acid | 241–242 |
| 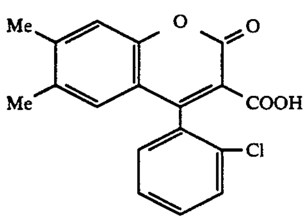 | 4-(2-chlorophenyl)-6,7-dimethyl-2-oxo-2H-1-benzopyran-3-carboxylic acid | 217–218 |
| 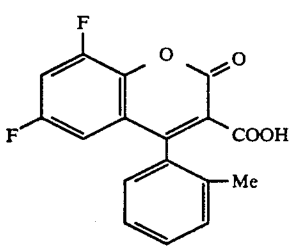 | 6,8-difluoro-4-(2-methylphenyl)-2-oxo-2H-1-benzopyran-3-carboxylic acid | 184–185 |
| 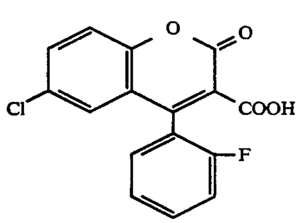 | 6-chloro-4-(2-fluorophenyl)-2-oxo-2H-1-benzopyran-3-carboxylic acid | 193–194 |
| 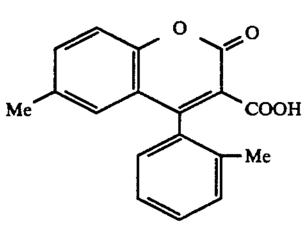 | 6-methyl-4-(2-methylphenyl)-2-oxo-2H-1-benzopyran-3-carboxylic acid | 207–209 |

TABLE 3-continued

| Structure | Chemical name | mp (°C.) |
|---|---|---|
| 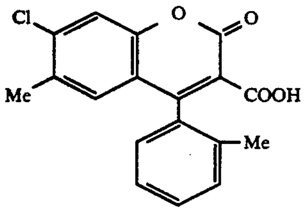 | 7-chloro-6-methyl-4-(2-methylphenyl)-2-oxo-2H-1-benzopyran-3-carboxylic acid | 254–255 |
| 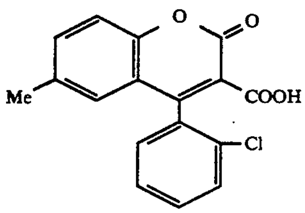 | 4-(2-chlorophenyl)-6-methyl-2-oxo-2H-1-benzopyran-3-carboxylic acid | 200–201 |
| 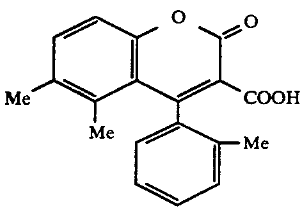 | 4-(2-methylphenyl)-5,6-dimethyl-2-oxo-2H-1-benzopyran-3-carboxylic acid | 240–241 |
| 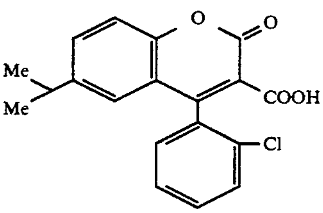 | 6-isopropyl-4-(2-methylphenyl)-2-oxo-2H-1-benzopyran-3-carboxylic acid | 155–156 |
| 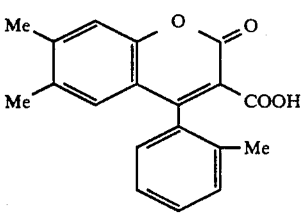 | 6,7-dimethyl-4-(2-methylphenyl)-2-oxo-2H-1-benzo benzopyran-3-carboxylic acid | 231–232 |
| 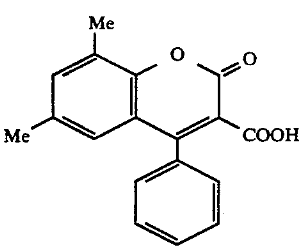 | 6,8-dimethyl-2-oxo-4-phenyl-2H-1-benzopyran-acid | 225–227 |
| 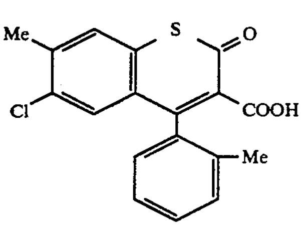 | 6-chloro-7-methyl-4-(2-methylphenyl)-2-oxo-2H-1-thiobenzopyran-3-carboxylic acid | 248–250 |

| Structure | Chemical name | mp (°C.) |
|---|---|---|
| (structure shown) | 4-(4-fluorophenyl)-6-isopropyl-2-oxo-2H-1-benzopyran-3-carboxylic acid | 219–221 |

REFERENCE EXAMPLE 3

A mixture of 2'-chloro-2-hydroxy-4,5-dimethylbenzophenone (2.6 g), diethyl malonate (3.2 g) and potassium fluoride (0.5 g) was heated for 12 hours at 170° C. to 180° C., and then subjected to silica gel chromatography, eluting with hexane-ethyl acetate (4:1), thereby affording ethyl 4-(2-chlorophenyl)-6,7-dimethyl-2-oxo-2H-1-benzopyran- 3-carboxylate as crystals (1.55 g, 43.5%). Recrystallization from ethanol gave colorless prisms.
mp: 130–131° C.
Elemental analysis for $C_{20}H_{17}ClO_4$:
Calculated: C 67.33; H 4.80.
Found: C 67.60; H 4.78.

The following compounds were obtained by the same procedure as in Reference Example 3. Ethyl 4-(2-chlorophenyl)-6-methyl-2-oxo-2H-1-benzopyran-3-carboxylate, mp: 135–136° C.
Ethyl 6-chloro-4-(2-fluorophenyl)-2-oxo-2H-1-benzopyran-3-carboxylate, mp:102–103° C.

REFERENCE EXAMPLE 4

A mixture of ethyl 6-chloro-4-(3,4-dimethoxyphenyl)-2-oxo-2H-1-benzopyran-3-carboxylate (1.0 g), dioxane (5 ml), ethanol (5 ml) and 2N-NaOH (12 ml) was refluxed for 1.5 hours, and then, adjusted to pH 2 by adding 2N-HCl. The mixture was stirred for 30 minutes at room temperature, to which water was added to obtain 6-chloro-4-(3,4-dimethoxyphenyl)-2-oxo-2H-1-benzopyran-3-carboxylic acid as crystals. Recrystallization from acetone gave colorless prisms (0.54 g, 58.1%).
mp: 235–236° C.
Elemental analysis for $C_{18}H_{13}ClO_6$:
Calculated: C 59.93; H 3.63.
Found: C 59.96; H 3.65.

REFERENCE EXAMPLE 5

1) To a mixture of 4-(2-methylphenyl)-6,7-dimethyl-2-oxo-2H-1-benzopyran-3-carboxylic acid (1.54 g), DPPA (1.65 g) and tert-butanol (20 ml) was dropwise added triethylamine (0.7 ml) under stirring. The mixture was stirred for 30 minutes at room temperature and refluxed for 3 hours. Then, the mixture was distilled to remove the solvent, and the residue to which water was added was extracted with ethyl acetate. The extract was washed with water, dried and distilled to remove the solvent, thereby affording 3-tert-butyloxycarbonylamino-4-(2-methylphenyl)-6,7-dimethyl-2H-1-benzopyran-2- one as crystals (1.6 g, 84.7%). Recrystallization from ethanol gave colorless prisms.
mp: 205–206° C.
Elemental analysis for $C_{23}H_{25}NO_4$:
Calculated: C 72.80; H 6.64; N 3.69.
Found: C 72.34; H 6.70; N 3.48.

2) To a solution of 3-tert-butyloxycarbonylamino-4-(2-methylphenyl)-6,7-dimethyl-2H-1-benzopyran-2-one (1.6 g) in dichloromethane (10 ml) was dropwise added trifluoroacetic acid (5 ml) under ice-cooling. The mixture was stirred for 30 minutes under ice-cooling and for 1.5 hours at room temperature and distilled to remove the solvent. The residue was neutralized by adding a saturated $NaHCO_3$ aqueous solution, thereby affording 3-amino-4-(2-methylphenyl)-6,7-dimethyl-2H-1-benzopyran-2-one as crystals (1.13 g, 95.8%). Recrystallization from methanol-chloroform gave colorless prisms.
mp: 229–230° C.
Elemental analysis for $C_{18}H_{17}NO_2$:
Calculated: C 77.40; H 6.13; N 5.01.
Found: C 77.62; H 6.18; N 4.99.

The following compounds were obtained by the same procedure as in Reference Example 5.
3-tert-Butyloxycarbonylamino-6-chloro-7-methyl-4-(2-methylphenyl)-2H-1-benzopyran-3-one, mp: 183–185° C.
3-Amino-6-chloro-7-methyl-4-(2-methylphenyl)-2H-1-benzopyran-3- one, mp: 212–213° C.
3-tert-Butyloxycarbonylamino-6,7-dimethyl-4-phenyl-2 2H-1-benzopyran-3- one, mp: 162–165° C.
3-Amino-6,7-dimethyl-4-phenyl-2H-1-benzopyran-3-one, mp: 162–163° C.

REFERENCE EXAMPLE 6

To a mixture of 5-chloro-4,2'-dimethyl-2-mercaptobenzophenone (4.0 g), triethylamine (2.43 g) and dichloromethane (40 ml) was dropwise added ethyl malonyl chloride (2.61 g) under ice-cooling. The mixture was stirred for 30 minutes under ice-cooling, washed with water, dried ($MgSO_4$) and distilled to remove the solvent. The oily substance was dissolved in benzene (40 ml), to which DBU (0.44 ml) was added. The mixture was refluxed for an hour, washed with water and dried ($MgSO_4$). After removing the solvent, the resulting residue was subjected to silica gel chromatography, eluting with hexane-ethyl ether (5:1). The eluent was distilled to remove the solvent, thereby affording ethyl 6-chloro-7-methyl-4-(2-methylphenyl)-2-oxo-2H-1-thiobenzopyran-3-carboxylate as crystals (1.25 g, 23.2%). Recrystallization from isopropyl ether gave pale yellow plates.
mp: 139–140° C.
Elemental analysis for $C_{20}H_{17}ClO_3S$:
Calculated: C 64.42; H 4.60.
Found: C 64.33; H 4.56.

REFERENCE EXAMPLE 7

A mixture of ethyl 6-chloro-4-(3,5-di-tert-butyl-4-hydroxyphenyl)-2-oxo-2H-1-benzopyran-3-carboxylate (2.0 g), 2N NaOH (11 ml) and ethanol (20 ml) was heated at 70° C. for 10 minutes. Then, the mixture was made acid with 2N HCl and extracted with ethyl acetate. The extract was washed with water and dried (MgSO4), and then, the solvent was removed to obtain 6-chloro-4-(3,5-di-tert-butyl-4-hydroxyphenyl)-2-oxo-2H-1-benzopyran-3-carboxylic acid as powders (1.3 g, 69.1%).

What we claim is:

1. A chromene derivative of the formula (I)

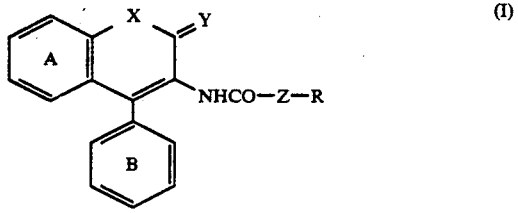

(I)

wherein
each ring of A and B is optionally substituted with 1 to 4 substituents selected from the group consisting of (1) halogen atom, (2) a straight or branched chain lower alkyl group of 1 to 6 carbon atoms which may be substituted with 2 to 5 halogen atoms, (3) a straight or branched chain lower alkyl group of 1 to 6 carbon atoms which may be substituted with 2 to 5 halogen atoms, (4) a straight or branched chain lower alkylthio group of 1 to 6 carbon atoms which may be substituted with 2 to 5 halogen atoms, (5) a nitro group, (6) a carboxy group, (7) a carboxy group esterified by an alkyl of 1 to 6 carbon atom, (8a $C_{1-3}$ acyloxy group, (9) a hydroxyl group and (10) a $C_{1-3}$ acyl group; X is an oxygen atom; Y is an oxygen or sulfur atom or denotes 2 hydrogen atoms; Z is a bond, —NH— or a saturated or unsaturated lower alkylene group and
R is (i) a straight, branched or cyclic chain alkyl group having 1 to 8 carbon atoms, (ii) an aryl group having 6 to 10 carbon atoms or (iii) an aralkyl group having 7 to 16 carbon atoms, wherein each of the groups of (i) and (ii) may be substituted with 1 to 5 substituents selected from the group consisting of (1) halogen atom, (2) a straight or branched chain lower alkyl group of 1 to 6 carbon atoms which may be substituted with 2 to 5 halogen atoms, (3) a straight or branched chain lower alkoxy group of 1 to 6 carbon atoms which may be substituted with 2 to 5 halogen atoms, (4) a straight or branched chain lower alkylthio group of 1 to 6 carbon atoms which may be substituted with 2 to 5 halogen atoms, (5) a nitro group, (6) a carboxy group, (7) a carboxy group esterified by a n alkyl of 1 to 6 carbon atoms, (8) a $C_{1-3}$ acyloxy group, (9) a hydroxy group and (10) a $C_{1-3}$ acyl group, or its salt.

2. A compound of claim 1 in which the ring A is substituted by one or two substituents selected from the group consisting of a halogen atom and a straight or branched chain lower alkyl group of 1 to 6 carbon atoms.

3. A compound of claim 1 in which the ring A is substituted by one or two substituents selected from the group consisting of chlorine, methyl, ethyl and i-propyl.

4. A compound of claim 1 in which the ring B is substituted by one, two or three substituents selected from the group consisting of a halogen atom, a straight or branched chain lower alkyl group of 1 to 6 carbon atoms and hydroxy group.

5. A compound of claim 1 in which the ring B is substituted by one, two or three substituents selected from the group consisting of chlorine, methyl, t-butyl and hydroxy.

6. A compound of claim 1 in which Z is —NH— and R is a phenyl group substituted by one, two or three substituents selected from the group consisting of a halogen, a straight or branched chain lower alkyl group of 1 to 4 carbon atoms, a straight or branched chain lower alkyl group of 1 to 4 carbon atoms and an acyloxy group of 1 to 4 carbon atoms.

7. A compound of claim 1 in which Z is —NH— and R is a phenyl group substituted by one, two or three substituents selected from the group consisting of chlorine, fluorine, methyl, methoxy and acetoxy.

8. A compound of claim 1 in which Y is an oxygen atom.

9. A compound of claim 1 which is N-[6-chloro-4-(2-methylphenyl)-2-oxo-2H-1-benzopyran-3-yl]-N'-(2,4-difluorophenyl) urea.

10. A compound of claim 1 which is N-(2,4-difluorophenyl)-N'-[6-isopropyl-4-(2-methylphenyl)-2-oxo-2H-1-benzopyran-3-yl] urea.

11. A compound of claim 1 which is N-(2,4-difluorophenyl)-N'-[4-(2-methylphenyl)-6,7-dimethyl-2-oxo-2H-1-benzopyran-3-yl] urea.

12. A compound of claim 1 which is N-[6-chloro-7-methyl-4-(2-methylphenyl)-2-oxo-2H-1-benzopyran-3-yl]-N,-(2,4-difluorophenyl) urea.

13. A compound of claim 1 which is N-[4-(2-chlorophenyl)-6,7-dimethyl-2-oxo-2H-1-benzopyran-3-yl]-N'-(2,4-difluorophenyl) urea.

14. A compound of claim 1 which is N-[7-chloro-6-methyl-4-(2-methylphenyl)-3-oxo-2H-1-benzopyran-3-yl]-N,-(2,4-difluorophenyl) urea.

15. A compound of claim 1 which is N-(4-acetoxy-3,5-dimethoxyphenyl)-N'-[4-(2-chlorophenyl)-6-methyl-2-oxo-2H-1-benzopyran-3-yl] urea.

16. A compound of claim 1 which is N-(4-acetoxy-3,5-dimethoxyphenyl)-N'-[6,7-dimethyl-4-(2-methylphenyl)-2-oxo-2H-1-benzopyran-3-yl] urea.

17. A compound of claim 1 which is N-(4-acetoxy-3,5-dimethoxyphenyl-N'-[6-chloro-7-methyl-4-(2-methylphenyl)-2-oxo-2H-1-benzopyran-3-yl] urea.

18. A compound of claim 1 which is N-(4-acetoxy-3,5-dimethylphenyl)-N'-[6-chloro-7-methyl-4-(2-methylphenyl)-2-oxo-2H-1-benzopyran-3-yl] urea.

19. An inhibitory composition for acyl-CoA:cholesterol acyltransferase which comprises an effective inhibitory amount of a chromene derivative of the formula (I) in claim 1 or its salt and a pharmaceutically acceptable carrier, diluent or excipient.

20. A method for preventing or treating hypercholesterolemia, atherosclerosis and the diseases caused thereby in mammals which comprises administering to a subject suffering therefrom an effective amount of a chromene derivative as claimed in claim 1 with a physiologically acceptable carrier.

21. A method for inhibiting acyl-CoA:cholesterol acyltransferase in mammals which comprises administering to a subject in need thereof an effective amount of a chromene derivative as claimed in claim 1 with a physiologically acceptable carrier.

* * * * *

UNITED STATES PATENT AND TRADEMARK OFFICE
CERTIFICATE OF CORRECTION

PATENT NO. : 5,278,186
DATED : January 11, 1994
INVENTOR(S) : Kanji MEGURO et al.

It is certified that error appears in the above-indentified patent and that said Letters Patent is hereby corrected as shown below:

In claim 1, column 29, line 27, change "alkyl" to --alkoxy--.
In claim 1, column 29, line 34, change "(8a" to --(8)a--.
In claim 1, column 29, line 55, change "a n" to --an--.
In claim 6, column 30, line 13, change "alkyl" to --alkoxy--.
In claim 12, column 30, line 33, change "N," to --N'--.
In claim 14, column 30, line 39, change "N," to --N'--.

Signed and Sealed this

Twentieth Day of December, 1994

Attest:

BRUCE LEHMAN

Attesting Officer     Commissioner of Patents and Trademarks